US00PP17415P2

(12) United States Plant Patent
Westhoff

(10) Patent No.: US PP17,415 P2
(45) Date of Patent: Feb. 13, 2007

(54) *PETUNIA* PLANT NAMED 'WESPECAMARIA'

(50) Latin Name: *Petunia×hybrida*
Varietal Denomination: Wespecamaria

(75) Inventor: Heinrich Westhoff, Südlohn (DE)

(73) Assignee: J.+H. Westhoff Interpel, Südlohn (DE)

( * ) Notice: Subject to any disclaimer, the term of this patent is extended or adjusted under 35 U.S.C. 154(b) by 20 days.

(21) Appl. No.: 11/151,888

(22) Filed: Jun. 14, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Petunia* plant named 'Wespecamaria', characterized by its cascading growth habit; freely branching habit; freely and continuous flowering habit; and single medium-sized bicolored flowers that are purple in color with white-colored margins with dark purple-colored venation.

1 Drawing Sheet

Botanical designation: *Petunia×hybrida.*
Cultivar denomination: 'Wespecamaria'.

BACKGROUND OF THE INVENTION

The present Invention relates to a new and distinct cultivar of *Petunia* plant, botanically known as *Petunia×hybrida,* and hereinafter referred to by the name 'Wespecamaria'.

The new *Petunia* is a product of a planned breeding program conducted by the Inventor in Südlohn, Germany. The objective of the breeding program is to create new *Petunia* cultivars with spherical growth habit, medium-sized flowers and attractive flower coloration.

The new *Petunia* originated from a planned cross-pollination made by the Inventor in 2000 of a proprietary *Petunia×hybrida* seedling selection identified as code number 99K7878, not patented, as the female, or seed parent, with a proprietary *Petunia×hybrida* seedling selection identified as code number 99Fa001, not patented, as the male, or pollen, parent. The new *Petunia* was selected by the Inventor from the progeny resulting from the stated cross-pollination in a controlled environment in Südlohn, Germany.

Asexual reproduction of the new cultivar by terminal cuttings in Südlohn, Germany since 2000, has shown that the unique features of this new *Petunia* are stable and reproduced true to type in successive generations.

SUMMARY OF THE INVENTION

Plants of the cultivar 'Wespecamaria' have not been observed under all possible environmental conditions. The phenotype may vary somewhat with variations in environment such as temperature, daylength, and light intensity without, however, any variance in genotype.

The following traits have been repeatedly observed and are determined to be the unique characteristics of 'Wespecamaria'. These characteristics in combination distinguish 'Wespecamaria' as a new and distinct *Petunia* cultivar:

1. Cascading growth habit.
2. Freely branching habit.

3. Freely and continuous flowering habit.
4. Single medium-sized bicolored flowers that are purple in color with white-colored margins with dark purple-colored venation.

Plants of the new *Petunia* differ from plants of the female parent selection in the following characteristics:

1. Plants of the new *Petunia* were more uniform than plants of the female parent selection.
2. Plants of the new *Petunia* had smaller flowers than plants of the female parent selection.
3. Plants of the new *Petunia* had lighter-colored flowers than plants of the female parent selection.

Plants of the new *Petunia* differ from plants of the male parent selection in the following characteristics:

1. Plants of the new *Petunia* were more freely branching than plants of the male parent selection.
2. Plants of the new *Petunia* had lighter green-colored leaves than plants of the female parent selection.
3. Plants of the new *Petunia* had darker-colored flowers than plants of the female parent selection.

Plants of the cultivar Wespecamaria can be compared to plants of the *Petunia* cultivar Wespecapur, described in U.S. Plant Pat. No. 15,342. However in side-by-side comparisons conducted in Südlohn, Germany, plants of the new *Petunia* and the cultivar Wespecapur, differed in the following characteristics:

1. Plants of the new *Petunia* had longer branches with shorter internodes than plants of the cultivar Wespecapur.
2. Plants of the new *Petunia* had shorter leaf petioles than plants of the cultivar Wespecapur.
3. Flower color of plants of the new *Petunia* was different than flower color of plants of the cultivar Wespecapur.
4. Plants of the new *Petunia* had shorter sepals than plants of the cultivar Wespecapur.
5. Plants of the new *Petunia* had shorter peduncles than plants of the cultivar Wespecapur.

Plants of the cultivar 'Wespecamaria' can also be compared to plants of the *Petunia* cultivar Bresh, disclosed in U.S. Plant patent application Ser. No. 09/592,379, now abandoned. However in side-by-side comparisons conducted in Südlohn, Germany, plants of the new *Petunia* and the cultivar Bresh differed in the following characteristics:

1. Plants of the new *Petunia* had thinner branches than plants of the cultivar Bresh.
2. Plants of the new *Petunia* had smaller leaves than plants of the cultivar Bresh.
3. Plants of the new *Petunia* and the cultivar Bresh differed in flower color.
4. Plants of the new *Petunia* had shorter peduncles than plants of the cultivar Bresh.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the colors of the new *Petunia.*

The photograph at the bottom of the sheet comprises a side perspective view of a typical plant of 'Wespecamaria'.

The photograph at the top of the sheet comprises a close-up view of a typical flower of 'Wespecamaria'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following botanical description were grown in 12-cm containers during the spring and summer for about 20 weeks in a glass-covered greenhouse and under conditions that closely approximate commercial production conditions in Südlohn, Germany. During the production of the plants, day temperatures ranged from 20 to 25° C., night temperatures ranged from 16 to 18° C. and light levels ranged from 3,000 to 50,000 lux.

Botanical classification: *Petunia×hybrida* cultivar Wespecamaria.

Parentage:

*Female parent.*—Proprietary *Petunia×hybrida* seedling selection identified as code number 99K7878, not patented.

*Male parent.*—Proprietary *Petunia×hybrida* seedling selection identified as code number 99Fa001, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Fine fibrous and well-branched.

Plant description:

*Form.*—Annual flowering plant; cascading plant habit. Viscid, glandular pubescent. Freely and continuous basal branching with lateral branches potentially forming at every node.

*Usage.*—Appropriate for hanging baskets, window boxes and patio containers.

*Plant height (from soil level to top of plant plane).*—About 22.7 cm.

*Plant diameter.*—About 25 cm.

*Stem description.*—Main branches, length: About 100 cm. Main branches, diameter: About 3.6 mm. Lateral branches, length: About 50 to 70 cm. Lateral branches, diameter: About 1.75 mm. Internode length: About 1.8 cm. Texture: Densely pubescent; viscid. Color: 144A.

*Foliage description.*—Arrangement: Before flowering, alternate; after flowering, opposite; simple. Length: About 4 cm. Width: About 2 cm. Shape: Ovate. Apex: Obtuse. Base: Attenuate. Margin: Entire. Aspect: Flat. Texture, upper and lower surfaces: Leathery; densely pubescent. Venation pattern: Pinnate. Color: Developing foliage, upper surface: 137A. Developing foliage, lower surface: 147B. Fully expanded foliage, upper surface: 146A to 146B. Fully expanded foliage, lower surface: 146B. Venation, upper and lower surfaces: 146C to 146D. Petiole length: About 7 mm. Petiole diameter: About 2.5 mm. Petiole color: 146D.

Flower description:

*Flower type and habit.*—Single salverform flowers; flowers face upward and outward; single, axillary. Freely flowering.

*Natural flowering season.*—Long day responsive; flowering from April until frost in the autumn in Germany; flowering continuous during this period.

*Fragrance.*—None detected.

*Flower longevity on the plant.*—About one week.

*Flower size.*—Diameter: About 4.7 cm. Depth (height): About 4.1 cm. Tube length: About 2.4 cm. Throat diameter, distal end: About 1.1 cm. Tube diameter, proximal end: About 2.5 mm.

*Flower buds.*—Length: About 3.2 cm. Diameter: About 4.5 mm. Shape: Oblong. Color: Towards the apex, 155A; mid-section, 148C; towards the base, N77C.

*Petals.*—Arrangement/appearance: Single whorls of five petals, fused into a flared trumpet. Length from throat: About 1.8 cm. Width: About 2.1 cm. Shape: Obtuse. Apex: Rounded to obtuse. Margin: Entire; undulate. Texture, upper and lower surfaces: Smooth, glabrous. Color: When opening, upper surface: N78A; margins, N155A; venation, N79A to N79B. When opening, lower surface: N82B; margins, N155A; venation, N79A to N79B. Fully opened, upper surface: N78B; margins, N155A; venation, N79A; color becoming closer to N80B with N79B venation. Fully opened, lower surface: 84A; margins, N155A; venation, N79A to N79B. Flower throat (inside): 79A to 79C; venation, N186A. Flower tube (outside): 79A to 79B; venation, N186A.

*Sepals.*—Arrangement/appearance: Single whorl of five sepals, fused at base; star-shaped. Length: About 1.5 cm. Width: About 4 mm. Shape: Oblong. Apex: Round to obtuse. Margin: Entire. Texture, upper and lower surfaces: Pubescent; leathery. Color, upper and surfaces: 146A to 146B.

*Peduncles.*—Length: About 2.1 cm. Width: About 1.5 mm. Strength: Wiry, strong. Texture: Pubescent. Color: 144A.

*Reproductive organs.*—Stamens: Quantity: About five per flower. Filament length: About 1.6 to 2.1 cm. Filament color: N77A to N77C. Anther shape: Four-parted, ovate. Anther length: About 2.8 mm. Anther width: About 2.1 mm. Anther color: N87C and N79B. Pollen amount: Abundant. Pollen color: 85B. Pistils: Quantity: One per flower. Pistil length: About 2.2 cm. Stigma shape: Ovate. Stigma color, immature: 147B. Stigma color, mature: 147B overlain with N77A. Style length: About 1.8 cm. Style color: 145C. Ovary color: 144B.

*Seed/fruit.*—Seed and fruit production have not been observed.

Disease/pest resistance: Plants of the new *Petunia* have not been noted to be resistant to pathogens or pests common to *Petunia.*

Temperature tolerance: Plants of the new *Petunia* have been observed to be tolerant to temperatures from 2 to 30° C.

It is claimed:

1. A new and distinct cultivar of *Petunia* plant named 'Wespecamaria', as illustrated and described.

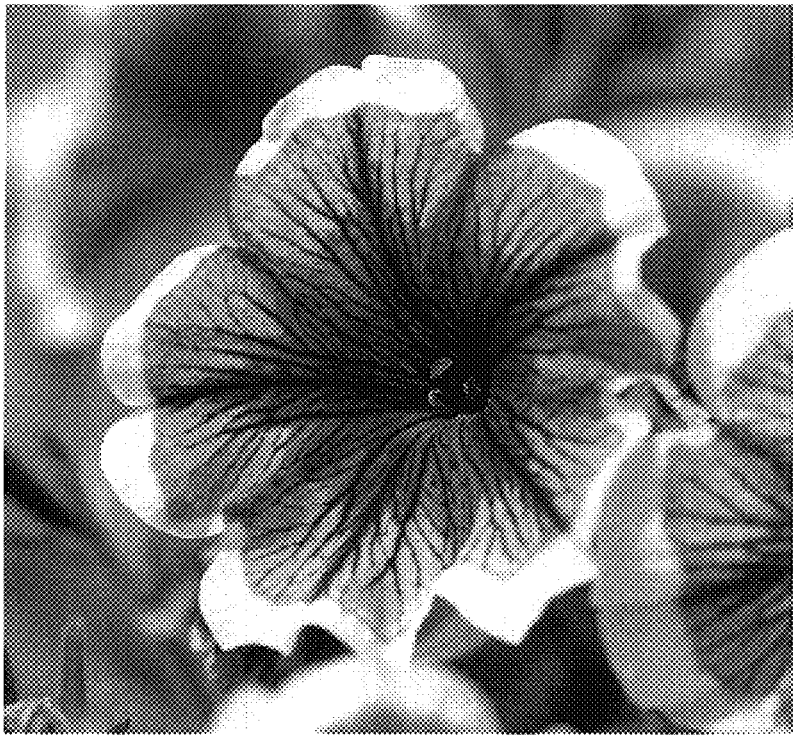
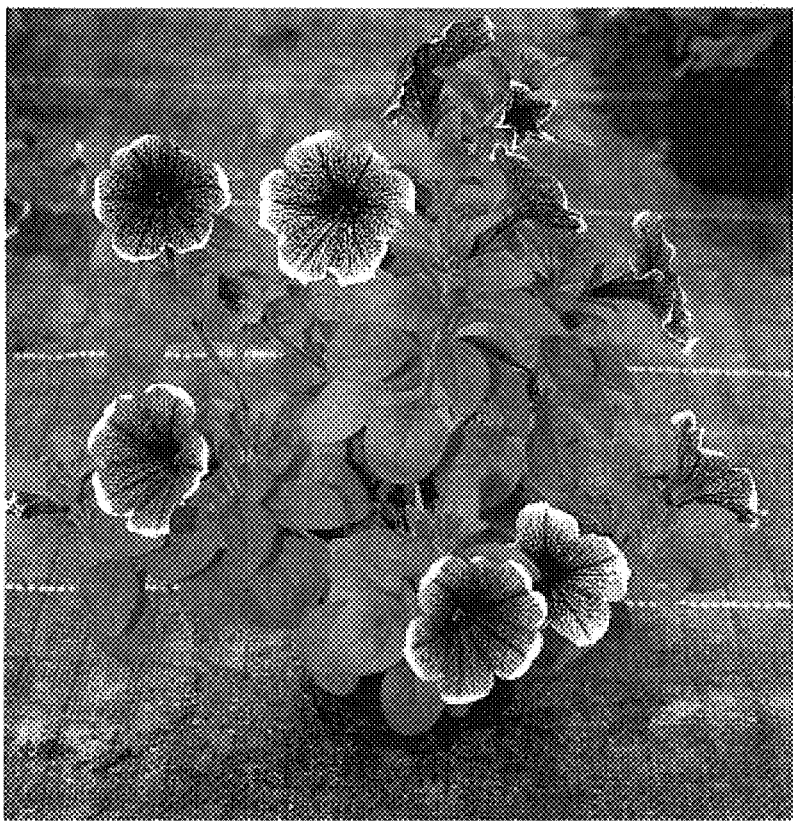

* * * * *